USO05554505A

United States Patent [19]
Hajek et al.

[11] Patent Number: 5,554,505
[45] Date of Patent: Sep. 10, 1996

[54] METHOD AND APPARATUS FOR OPTICALLY SCREENING MICROSCOPIC CELLS

[75] Inventors: Constance M. Hajek, Miami Lakes; Thomas Russell, Miami, both of Fla.

[73] Assignee: Coulter Corporation, Miami, Fla.

[21] Appl. No.: 160,986

[22] Filed: Dec. 1, 1993

Related U.S. Application Data

[63] Continuation of Ser. No. 782,155, Oct. 24, 1991, abandoned, which is a continuation-in-part of Ser. No. 617,096, Nov. 23, 1990, Pat. No. 5,340,719.

[51] Int. Cl.$^6$ .......................... G01N 33/50; G01N 33/80; G01N 1/28; G01N 21/00
[52] U.S. Cl. .......................... 435/721; 435/7.2; 435/7.23; 435/7.24
[58] Field of Search .................................. 435/7.2, 7.21, 435/7.23, 7.24

[56] References Cited

U.S. PATENT DOCUMENTS

| | | | |
|---|---|---|---|
| 4,029,470 | 6/1977 | Wilkins et al. | 8/94.11 |
| 4,115,535 | 9/1978 | Giaver | 436/526 |
| 4,342,739 | 8/1982 | Kakimi et al. | 435/7.9 |
| 4,483,928 | 11/1984 | Suzata et al. | 436/519 |
| 4,511,662 | 4/1985 | Baran et al. | 436/513 |
| 4,615,878 | 10/1986 | Kass | 424/3 |
| 4,714,606 | 12/1987 | Kass | 424/3 |
| 5,006,459 | 4/1991 | Kung et al. | 435/5 |
| 5,340,719 | 8/1994 | Hajek et al. | 435/7.21 |
| 5,348,859 | 4/1994 | Brunhouse et al. | 435/7.24 |

FOREIGN PATENT DOCUMENTS

| | | | |
|---|---|---|---|
| 60-157050 | 8/1985 | Japan | 435/7.24 |
| 2105463 | 3/1983 | United Kingdom | 435/7.2 |
| 8806918 | 9/1988 | WIPO | 435/7.2 |

OTHER PUBLICATIONS

King, M. A., 1984, Journal of Immunological Methods, 72:481–488.
Kvalheim, G., et al., 1988, Bone Marrow Transplantation, 3:31–41.
Kickler, T. S., et al., 1990, Blood, 76(4)849–852.
Burkhardt, J. J., et al., 1982, Blood, 60(3):767–771.
Sthoeger, D., et al., 1990, American Journal of Hematology 34:275–282.
Sato, T., et al., 1989, British Journal of Haematology, 72:184–190.

(List continued on next page.)

Primary Examiner—Robert A. Wax
Assistant Examiner—William W. Moore
Attorney, Agent, or Firm—John T. Winburn

[57] ABSTRACT

An optical screening method and apparatus for identifying both the morphology and selected characteristics or properties expressed by cells, such as cancer cells. The cells are combined with one or more different sets of microspheres, each set having a reactant bond thereto which will bind to a specific molecule which can exist on one or more types of cancer cells. The cells and microspheres are formed as a smear on a slide, stained with a histological type stain and optically viewed to identify the type of cells to which the different sets of microspheres do or do not bind. The different sets of microspheres are optically differentiated by having different optical characteristics, such as size, shape, color or combinations thereof. A fast cancer cell screening method or panel is provided by adding different sets of microspheres having different reactants bound thereto to different sample portions and optically screening the different sample smears. The microspheres also can be removed from a sample portion with any cells bound thereto and compared to another non-modified sample portion to ascertain if the cancer cells of interest have been removed from the sample portion.

38 Claims, 13 Drawing Sheets

OTHER PUBLICATIONS

Kernohan, N. M., et al., 1990, Journal of Pathology; 161:35–40.

Dowell, B. L., et al., 1984, Developmental and Comparative Immunology, 81:187∝1495.

Brando, B., et al., 1988, Transactions of the America Society for Artificial Internal Organs, 34:441–444.

Lippi, U., et al., 1990, American Journal of Coagulation Physiology, 93(6):760–764.

Zeleznik, N. J., et al., 1986, Journal of Cellular Biochemistry, *Supplement IOC:* p. 144, Abstract L131.

METHOD AND APPARATUS FOR OPTICALLY SCREENING MICROSCOPIC CELLS

CROSS REFERENCE TO RELATED APPLICATION

This application is a continuation of application Ser. No. 07/782,155, filed Oct. 24, 1991, which is a continuation-in-part of copending application U.S Ser. No. 07/617,096, filed Nov. 23, 1990, entitled METHOD AND APPARATUS FOR OPTICALLY SCREENING MICROSCOPIC CELLS, the disclosure of which is incorporated by reference.

BACKGROUND OF THE INVENTION

This invention relates generally to a method and apparatus for identifying or screening cells for research or diagnostic purposes. More particularly, the invention is directed to optically identifying cells which have the presence or absence of specific surface molecules, while viewing the morphological characteristics of the cells utilizing conventional staining procedures, for example, such as for cancer screening.

Stained cells are the basis of conventional cell morphology study. Typically the cells are placed on a slide, and then stained, where they are optically or visually viewed through a microscope. The optical or visual information from microscopic images also can be utilized in automatic scanning devices such as image analyzers.

In the late 19th century, Ehrlich reported on the morphology, physiology and pathology of blood cells, which advanced hematology into a new era by establishing methods of detecting and differentiating the leukemias and anemias. Ehrlich observed that acidic, basic and neutral dyes react specifically with such cellular components as granules and nuclei of white blood cells (WBC).

Romanowsky continued these advancements in hematology by developing a polychromatic stain for use on cells. Currently, Wright's Stain, a modification of Romanowsky's stain is conventionally utilized to visually examine cells. Peripheral blood smears are stained and routinely visually examined for abnormal morphologic variations. Classification of the types of cells and the stages of cell differentiation are key factors in identifying a disease process. Despite the utilization of automated hematology analyzers and flow cytometry instruments, there remains a need for direct visual (microscopic) evaluation of the cells.

Immunologic studies also are important when anomalies are found on a peripheral blood smear. It is necessary to determine the specific subtype of the leukemia in order to better select a treatment method for the disease and to provide the patient with as specific a prognosis as possible. For example, in forms of acute leukemia, there is a predominance of blasts in the peripheral blood. These immature cells can be difficult to classify as either lymphocytic or granulocytic because of the lack of differentiation. If the blast subpopulation that is rapidly proliferating is found to be T11 receptor bearing, the leukemia can be classified as an acute lymphoblastic leukemia (ALL), T-cell type. In general, T lineage ALL has a poorer prognosis than B lineage ALL. Further subgrouping these leukemias according to their level of differentiation is also customary. Groups I and II exhibit antigens that are seen on early thymic precursor cells; while those expressed in Group III are similar to the surface antigens found on mature T cells.

Immunology experiments were first developed utilizing a light microscope for determination of lymphocyte subsets. Rosette formation between human lymphocytes and sheep red blood cells (RBC) was observed by Coombs and others in 1970. Later studies found that all or at least a major portion of thymus-derived lymphocytes (T-cells) under the proper conditions displayed the rosette formation phenomenon. These studies utilized Ficoll isolated lymphocytes and were for a period of time routinely employed for subset classification of isolated lymphocytes utilizing a light microscope.

Lymphocyte subsets now conventionally are determined by fluorescent labeling of the cells, in a sample with a fluorescent-tagged monoclonal antibody. The fluorescent-tagged monoclonal antibody binds to the antigen of interest on the surface of the cells expressing the antigen. The cell sample then is analyzed by utilizing a fluorescent microscope or by utilizing a highly sophisticated flow cytometry instrument. When utilizing a flow cytometry instrument, the cell sample preparation, data collection and data analysis must be performed by a specially trained technician. The flow cytometry instrument includes a laser and complex optical system, a high-power computer and electrical and fluidic systems. The component systems of the flow cytometry instrument must be properly maintained and calibrated on a regular and frequent basis. Although the flow cytometry instrument currently is the reference lymphocyte subset determination or cancer immunophenotyping method, the method has several drawbacks including the high cost of the instrument and the expertise required to correctly operate such instrument. The flow cytometry method is further disadvantageous to the general pathologist since only large facilities can justify the cost of a flow cytometry instrument. Further, sending samples to another facility for a flow cytometry analysis often causes a delay of three (3) or more days in obtaining useful results. It therefore would be most advantageous to have a screening method which is fast, inexpensive, simple and readily available to the general pathologist.

Lymphocyte subsets also can be determined utilizing automated instruments and methods developed by the assignee of the present application, Coulter Electronics, Inc. An improved simple automated instrument and methods of using the same is disclosed in application U.S. Ser. No. 587,646, filed Sep. 20, 1990, now U.S. Pat. No. 5,223,398, entitled AUTOMATED ANALYZER AND METHOD FOR SCREENING CELLS OR FORMED BODIES FOR ENUMERATION OF APPLICATIONS EXPRESSING SELECTED CHARACTERISTICS, which is a continuation of U.S. Ser. No. 025,345, filed Mar. 13, 1987 of the same title. This application combines the application of electronic sensing aperture principles, the specificity of selected biological molecules for identifying and/or enumerating defined populations of cells or formed bodies and microscopic particle technology. The automated analyzer can be used together with a special lysing reagent and/or antibodies coupled to microscopic microspheres or supports of varying composition.

A second application, U.S. Ser. No. 07/849,481, filed Mar. 10, 1992, which is a continuation of U.S. Ser. No. 285,856, filed Dec. 16, 1988, entitled METHOD AND APPARATUS FOR SCREENING CELLS OR FORMED BODIES WITH POPULATIONS EXPRESSING SELECTED CHARACTERISTICS, discloses the screening of direct subsets from whole blood samples or portions thereof.

A third application, U.S. Ser. No. 07/929,156, filed Aug. 12, 1992, now U.S. Pat. No. 5,231,005, which is a continuation of U.S. Ser. No. 339,156, filed Apr. 14, 1989, now U.S. Pat. No. 5,260,192 entitled METHOD AND APPARATUS FOR SCREENING CELLS OR FORMED BODIES WITH POPULATIONS EXPRESSING SELECTED CHARACTERISTICS UTILIZING AT LEAST ONE SENSING PARAMETER, discloses multipart or five part white blood cell differentials, lymphocyte subsets and overlapping determinations performed from a whole blood sample or from a sample with the red blood cells and/or populations of the white blood cells removed by elimination of populations and/or subsets thereof with one or more light or electronic parameters.

A fourth application, U.S. Ser. No. 07/525,231, filed May 17, 1990, entitled METHOD AND APPARATUS FOR SCREENING OBSCURED OR PARTIALLY OBSCURED CELLS, discloses an analysis of obscured cells by utilizing microspheres having specific monoclonal antibodies bound thereto to move the sensed characteristics of the obscured cells from one cell population to another. Each of the above four referenced applications is incorporated herein by reference.

The method and apparatus embodying the invention can be utilized with a variety of immunological reactions, such as immunological reactions involving reactants and formed bodies or cells. The invention also applies to analyses of formed body suspensions such as some bacteria and viruses among others. As utilized herein, cells are defined as animal or plant cells, including cellular bacteria, fungi, which are identifiable separately or in aggregates. Cells are the least structural aggregate of living matter capable of functioning as an independent unit. For example, cells can be human red blood cells (RBC) and WBC populations, cancer or other abnormal cells from tissue or from blood samples. Formed bodies are defined as some bacteria and viruses. The cells and formed bodies suitably tagged or labeled, reasonably can be expected to be optically identified by the method and apparatus of the invention in the same manner as the human blood cell examples.

Although the term "reactant" has been utilized in the above applications to define lysing agents and monoclonal antibodies, reactants can include various agents which detect and react with one or more specific molecules which are on the surface of a cell or formed body. Some examples are given below:

| Reactant | Specific Molecule |
| --- | --- |
| Antibody | Antigen |
| Drug | Drug Receptor |
| Hormone | Hormone Receptor |
| Growth Factor | Growth Factor Receptor |

The reactants couple or bind to the specific molecule(s) on the cells. These reactants do form part of a chemical reaction; however, the reactants are not necessarily chemically altered.

One prior art procedure of lymphocyte subset determination utilizes a light microscope and antibody-labeled microspheres. This procedure is available from Bio-Rad Laboratories of Richmond, Calif. The procedure is available to identify T and B lymphocytes. The antibody-labeled microspheres are utilized to bind to the cells which exhibit the surface antigen of interest. Two different colored antibody-labeled microspheres are utilized to differentiate the T and B lymphocytes. The microscopist identifies the cells positive for a particular antigen by the presence of the antibody-labeled microspheres bound to the cells. Cells which do not have an antibody-labeled microsphere bound thereto represent the negative cell population, not expressing the antigen(s) of interest. This procedure is limited by the fact that the lymphocytes must first be isolated from a whole blood sample, utilizing an isolation medium, such as Ficoll-Hypaque. Granulocyte contamination can lead to falsely elevated non-positive cell values and an increased number of phagocytic cells. Further, only lymphocyte subset determinations can be performed, since the remaining cells from a whole blood sample first are eliminated. Also, the cell morphologic evaluation is limited since the cells are not stained with the conventional Romanowsky or Wright type stain, but merely are stained to determine the cell viability. The morphologic evaluation is further limited since the cells are evaluated in a suspension and are not evaluated on slides, as is conventional.

SUMMARY OF THE INVENTION

The invention provides a method and apparatus for optically screening cells to identify the morphology and selected characteristics or properties expressed by the cells. The cells are combined with one or a plurality of different sets of microspheres, each set having a reactant bound thereto which will bind to a specific molecule which can exist on one or more types of the cells. The cells and microspheres are prepared as a smear on a slide and stained with a Wright type stain. The cells then are optically viewed by an operator and/or automatically, to identify the type of cells, if any, to which the different microspheres are bound.

The sample can be any suspension of cells such as from a whole blood sample or portion thereof and the RBC's can be removed or left intact in the sample. The sets of microspheres can be combined separately or concurrently in the same or different sample portions and preferably are mixed therewith. The different sets of microspheres have different optical characteristics to be optically differential. The different optical characteristics between the sets can be color, size, shape or a combination thereof.

Where a blood sample includes a high number of cells positive for a specific antigen, clumping of the cells can occur. The clumping can be observed visually or optically as a fast screening procedure. The clumping is observed as an aggregate rim in mixing vessels or a microscopic agglutination on slides.

The cells also can be optically screened utilizing a first reactant which will bind to a specific molecule on one or more types of cells. As one example, the first reactant may be obtainable in insufficient concentrations to be bound first to a set of microspheres. In such case the first reactant can be combined with the cells to bind thereto and then a set of microspheres having a second reactant bound thereto can be added to the first reactant cell mixture. In this case the second reactant is a type which will bind to the first reactant to bind the microspheres to the cells. The first reactant and second reactant bound to microspheres also can be combined with the cells simultaneously. Also, the second reactant bound to the microsphere can be combined with the first reactant to bind the first reactant to the second reactant and then the microspheres with the first and second reactant bound thereto can be combined with the cells.

The specific molecules can be those of cancer cells present in the sample. The cancer cells can be identified by one or a plurality of different sets of microspheres, in one or more sample smears. This provides a simple, yet rapid method for obtaining cancer screening information to be utilized by the pathologist for treatment, prognosis or for elimination of one or more further smear or other flow cytometry testing procedures.

DETAILED DESCRIPTION OF THE PREFERRED EMBODIMENTS

Figure 1:
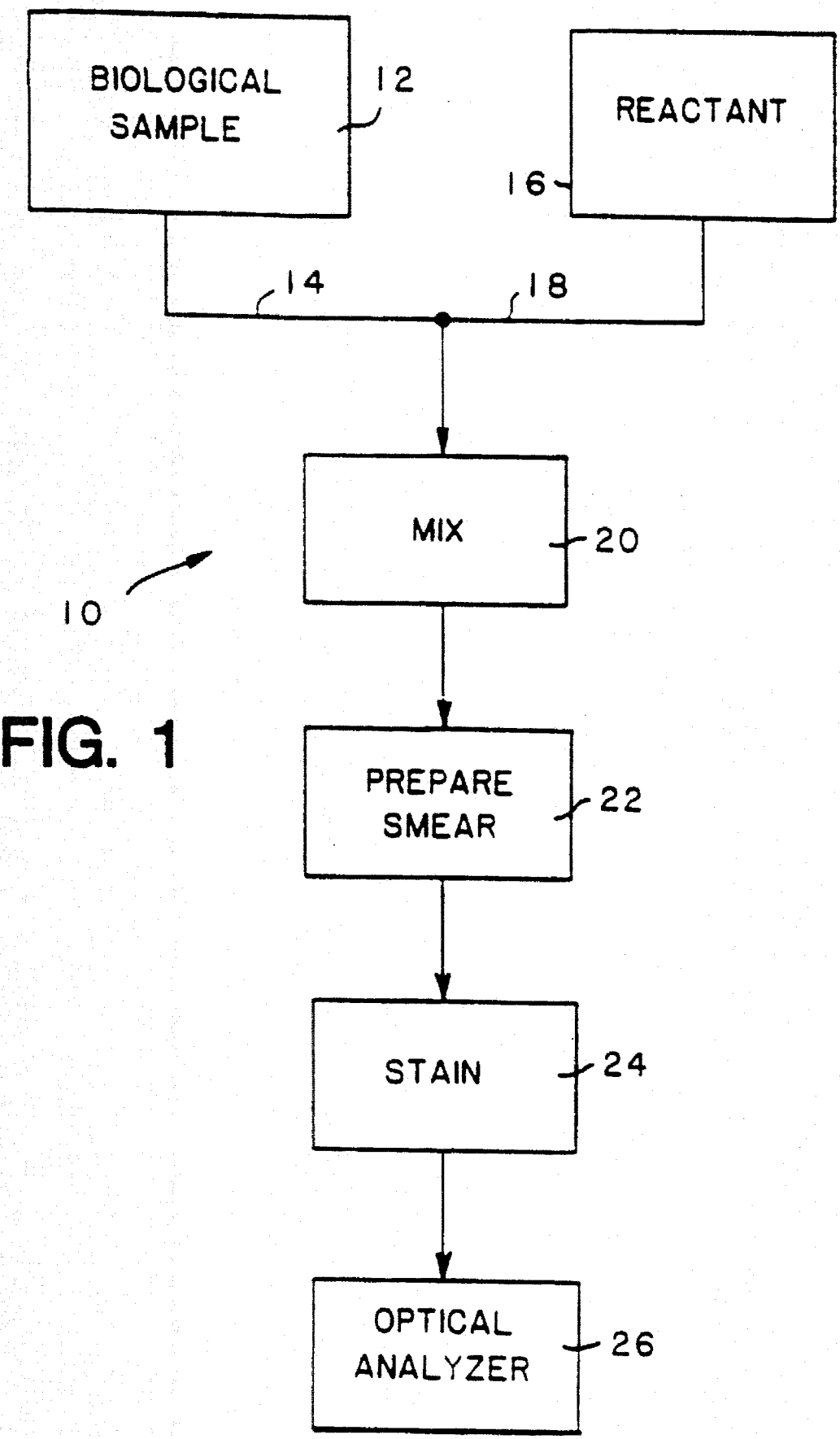
FIG. 1 is a schematic block diagram of one optical screening analyzer embodiment of the present invention.

Referring to FIG. 1, a first optical cell screening embodiment of the present invention, is designated generally by the reference character 10. The optical cell screener 10 includes a biological sample 12, which contains at least a first set of biological cells (not illustrated), such as in or from a whole blood sample.

The sample 12 is combined via a line 14 with at least one reactant 16 via a line 18. The reactant 16 can include a chelating agent, such as standard EDTA added to the sample 12 as a blood anticoagulating agent and to prevent the neutrophils (N's) from ingesting the microspheres.

The reactant 16 also includes a plurality or first set of microspheres, having an antibody specific to a particular antigen which can exist on at least one type of cell bound thereto. For blood, the cells express antigens to which a specific antibody or antibodies will bind. In general, antigens are molecules as are the antibodies which will bind thereto, and therefor for blood or other viable cells, the reaction can be specified as a first type of molecule which chemically interacts specifically with a second type of molecule. The combined sample 12 and the reactant 16 then preferably are mixed by a functionally designated mixing station 20. A portion of the mixture then is placed on a slide and a smear is prepared therefrom by a functionally designated smear preparing station 22. The smear then is stained in a functionally designated staining station 24.

The stain should be one of the groups of histological stains, which are utilized to differentiate various cell characteristics. For blood cells, the stain preferably is a so-called "Wright" type stain, as previously described, the stain allows the morphology of the cells to be differentiated under a microscope in a conventional matter. Some other types of histological stain examples useful in the procedures of the present inventions are Hematoxylin, Gentian Violet and Giemsa Blood Stain. Hematoxylin is utilized as a general tissue stain for animal histology designed to show nuclei. Gentian Violet is utilized as a bacterial stain designed to show capsules. Giemsa Blood Stain is utilized to show differentiation of types of leukocytes, rickettsiae, bacteria and inclusion bodies. The stained slide then is optically viewed at an optical analyzer 26. The cells on the slide are optically screened to determine which types of cells have the microspheres bound thereto. This identifies the presence or absence of specified receptors or antigens on the cells and hence the status of the sample, as will be further described hereinafter.

Figure 2:
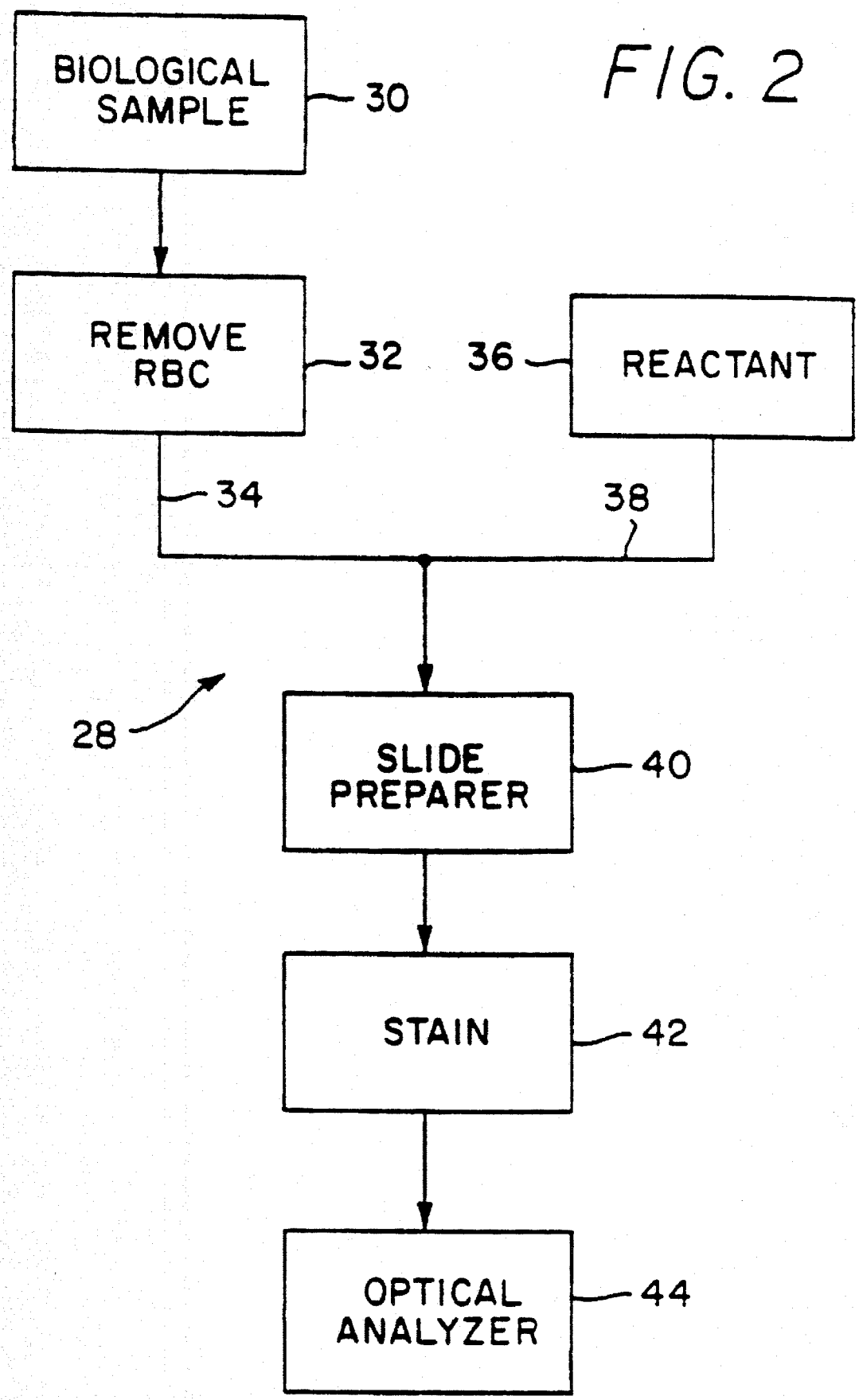
FIG. 2 is a schematic block diagram of a second optical screening analyzer embodiment of the present invention.

In the optical screening instrument 10, the sample 12 is either a whole blood sample and the red blood cells (RBC's) are left therein or the sample 12 is only a portion of a whole blood sample which may or may not include platelets or RBC's and all the WBC populations. A second optical cell screener embodiment of the present invention is designated generally by the reference character 28, referring to FIG. 2. The optical cell screener 28 includes a biological sample 30, which can be a whole blood sample or can be a blood sample at least including WBC's. The biological sample 30 also can be derived from other biological fluids or tissue, bone marrow, urine, spinal or pleural fluids or lymph glands.

The RBC's can be removed from the mixture by a functionally designated RBC removing station 32, when desired. The RBC's can be removed from the mixture by the station 32 in a number of ways. The RBC's can be lysed by a lyse. One such preferential lyse and a quench which can be utilized therewith is described hereinafter. The RBC's also can be removed utilizing a plurality of magnetic microspheres with an antibody specific to the RBC's bound to the microspheres (not illustrated). The bound RBC's are held in a magnetic field, while the remaining sample is removed to remove the RBC's. For example, one particular RBC specific antibody which can be utilized is disclosed in U.S. Pat. No. 4,752,563, entitled MONOCLONAL ANTIBODY FOR RECOVERY OF LEUKOCYTES IN HUMAN PERIPHERAL BLOOD AND METHOD OF RECOVERY EMPLOYING SAID MONOCLONAL ANTIBODY, which is incorporated herein by reference. A buffer can be included in addition to or in place of the sample buffer. A combination of the preferential RBC lyse and the RBC specific microspheres also can be utilized. Details of the RBC removal can be found in the four incorporated instrument applications of the assignee of the present invention, cited on pages 3 and 4 herein.

The sample 30 then is combined via a line 34 with a reactant 36 via a line 38. The combined sample 30 and reactant 32, preferably are mixed together. Specific details of an appropriate mixing apparatus which can be utilized herein are disclosed in Ser. No. 517,309, filed May 1, 1990 now U.S. Pat. No. 5,238,812, entitled METHOD AND APPARATUS FOR RAPID MIXING OF SMALL VOLUMES FOR ENHANCING BIOLOGICAL REACTIONS, which is a continuation of Ser. No. 025,337, filed Mar. 13, 1987 of the same title, which are incorporated herein by reference. By utilizing the mixer the reactions can be enhanced in speed without significantly damaging the properties of interest of the cells, if desired. The mixer 20 could utilize the same type of mixing apparatus, but also can be other types of gentle mixing apparatus, such as a simple roller rocker, since reaction speed is not necessarily critical.

A portion of the RBC removed mixture then is concentrated as a smear on a slide by a slide preparing station 40. Once the slide is prepared by concentrating the cells of interest and removing the excess moisture, such as by slide centrifugation, the slide is stained as before in a stain station 42. The stained slide then again is optically analyzed by an analyzer 44, which can be the same as the analyzer 26.

The optical cell screener 28 has been described with the removal of the RBC's prior to mixing with the reactant 36. In general this is preferable for use when removing the RBC's with magnetic microspheres. This also allows fewer microspheres of interest to be utilized, since the RBC's are removed and cannot interfere with the binding of the microspheres. When utilizing lyse, it is preferable to remove the RBC's after the reactant 36 and sample 30 are combined, so that the cells are exposed to the lyse for a shorter period of time.

Figure 3:
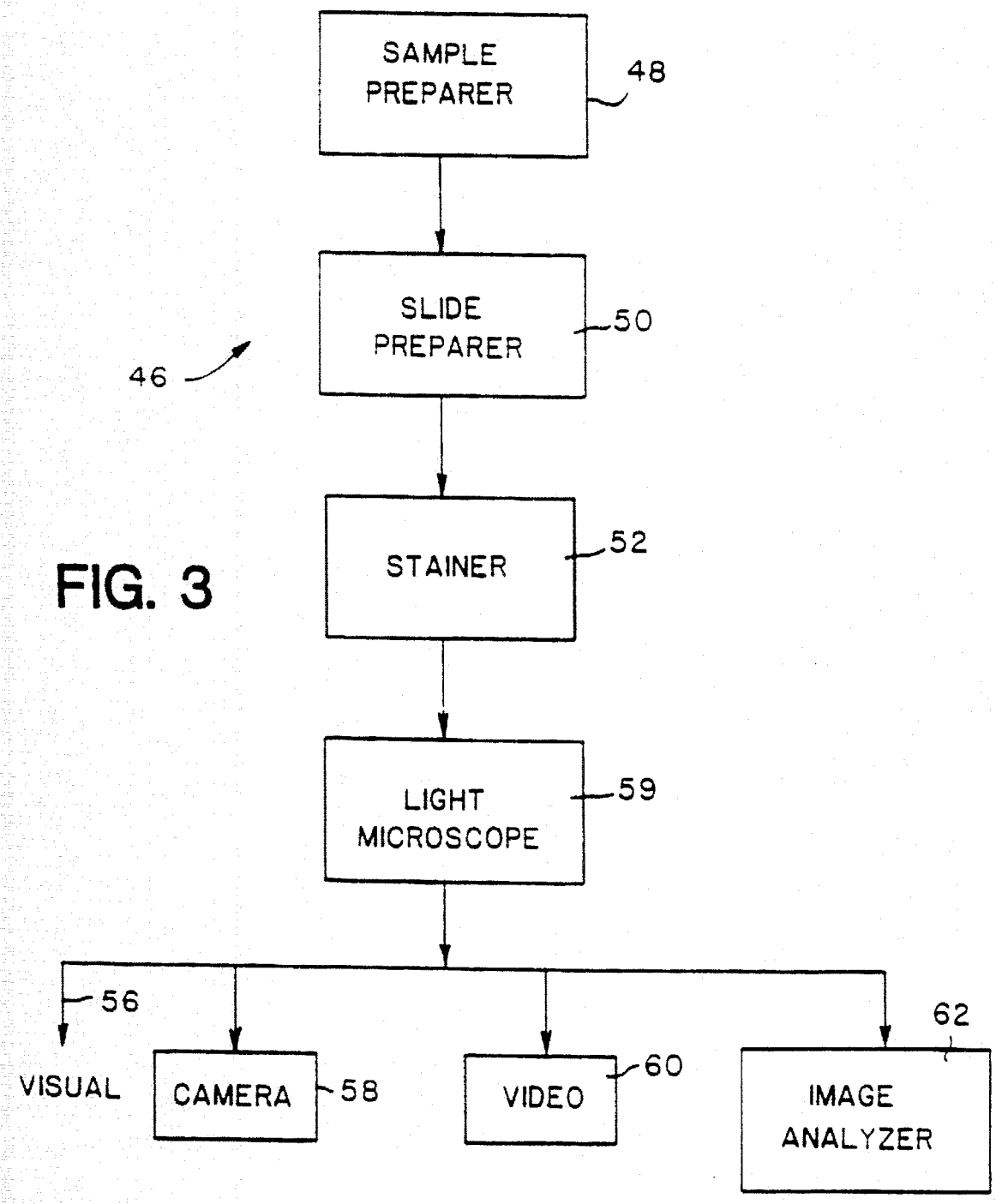
FIG. 3 is a block diagram of a specific optical screening analyzer embodiment of the present invention.

An automated or semi-automated optical cell screener embodiment is illustrated in FIG. 3, designated generally by the reference character 46. The optical cell screener 46 includes a sample preparer 48, which can eliminate RBC's or platelets if desired and add one or more different sets of microspheres with different antibodies bound thereto, which are specific to different antigens which can exist on one or more types of cells in the sample. The sample preparer 48 preferably also will combine and preferably will mix the sample and microspheres to provide rapid binding of the cells and microspheres.

An aliquot or portion of the prepared sample then is formed as a smear on a slide by a slide preparer 50. The slide preparer 50 can be either a conventional slide preparer of a slide containing the RBC's or a slide spinner for a sample with the RBC's removed.

The slide then is stained in a stainer 52. Once the slide is stained, the sample can be optically viewed or analyzed utilizing a light microscope 54. The light microscope 54 can have numerous outputs, a visual output 56 for a user's eyes, a camera output 58 for taking photographs of the cells and microspheres, a video output 60 which can be viewed by users other than the user of the visual output 56 and from which scanning tapes can be made and an image analyzer output 62, which automatically can scan and identify both the morphology of the cells and the color and/or size of the microspheres. Numerous types of conventional image analyzers can be utilized, such as those sold by Inovision Corp. Research Triangle Park, North Carolina, and the Bio Vision workstation sold by Perceptics Corporation, Knoxville, Tenn.

For blood samples, each biological sample contains at least a first set of biological cells (not illustrated), including at least one white blood cell population having at least one definable subset, such as in or from a whole blood sample. As utilized herein, WBC subsets are subsets of a WBC population to which specific monoclonal antibodies can be bound. A nomenclature now has been defined for the monoclonal antibodies by the World Health Organization and the International Immunology Society. The monoclonal antibodies are defined by a cluster designation (CD) nomenclature which defines a particular specificity for a cell or group of cells and the monoclonal antibodies specific for that CD group. For example purposes only, certain CD groups have been utilized in the following examples. The CD nomenclature, specificity and some commercial sources of monoclonal antibodies are illustrated in Table I.

TABLE I

| Cluster of Differentiation | Antibody (Commercial Source) | Specificity |
|---|---|---|
| CD2(gp 50)[a] | T11 (Coulter)[b] OKT11 (Ortho); Leu5a (BD) | E Rossette Receptor |
| CD4(gp 56) | T4 (Coulter) OK4$_a$ (Ortho); Leu3a (BD) | Helper/inducer T |
| CD5(gp 67) | T1 (Coulter) | All mature T-cells mature thymocytes, B-cell subsets |
| CD7(gp 40) | 3A1 (Coulter) | T-cells, most T-ALL |
| CD8 (gp 32-33) | T8 (Coulter) OKT8 (Ortho); Leu2a (BD) | Cytotoxic/ Suppressor T |
| CD10(gp 100) | J5 (Coulter) Anti-CALLA (BD) | Common Acute Lymphoblastic Leukemia Antigen pre-B cells, granulocytes |
| CD13(gp 150) | MY7 (Coulter) | Monocytes, granulocytes, CF11-6 |
| CD14(gp 55) | MO2, MY4 (Coulter) | Monocytes, few granulocytes |
| CD19(gp 95) | B4 (Coulter) | Pan B cell, pre-B ALL |
| CD20(gp 35) | B1 (Coulter) Leu 16 (BD) | All B cells except for plasma cells, B cell tumors, except for myeloma, some non-T ALL cells |
| CDw29(gp 135) | 4B4 (Coulter) | Helper/ inducer T |
| CD33(gp 67) | MY9 (Coulter) | Early myeloid progenitors, myeloid cells, AML |
| CD34(gp 115) | HPCA-1 (BD) | Myeloid progenitors |
| CD41(p130,115)[c] | PLT-1 (Coulter) | Platelets and megakaryocytes |

[a]gp — glycoprotein, molecular weight in kilodaltons
[b]Coulter — Coulter Immunology Division of Coulter Corporation (Hialeah, Florida)
BD — Becton-Dickinson Immunocytometry Systems
Ortho — Ortho Diagnostic Systems (Raritan, New Jersey)
[c]p — protein, molecular weight in kilodaltons Additionally, three other antibodies are utilized for example purposes, which do not yet have CD nomenclatures. One antibody is an N specific antibody disclosed in U.S. Pat. No. 4,931,395, entitled MONOCLONAL ANTIBODY SPECIFIC TO NEUTROPHILS. The second antibody is an N and E specific antibody (KC-48) disclosed in U.S. Pat. No. 4,865,971, entitled MONOCLONAL ANTIBODY SPECIFIC TO A COMMON DETERMINANT SITE OF NEUTROPHILS AND EOSINOPHILS, both of which are incorporated herein by reference. The third antibody is a so-called HLA-DR (p29/34), such as I3 provided by Coulter which has a specificity to MHC Class II HLA DR, monocytes, macrophages, B cells and activated T-cells.

Although, not all of the CD examples have more than one commercial source listed, virtually all of the CD examples can be obtained from more than one of the above listed or other readily identifiable commercial sources.

The magnetic microspheres utilized can be of any suitable type and in the examples are polystyrene magnetic microspheres of 0.7 and 1.3 micron diameter, with a weight to volume of 10% solids, sold by Bangs Laboratories of Carmel Indiana. The non-magnetic microspheres again can be of any suitable type and in the examples are surfactant free sulfated polystyrene latex microspheres of 1.05, 2.17 and 3.06 micron diameter with a weight to volume of 8% solids, sold as IDC microspheres by Interfacial Dynamics of Portland, Oreg.

Although these specific microspheres are utilized for example purposes, other types and sizes of microspheres from other conventional sources also can be utilized. In general it is preferable to utilize microspheres of a 5 micron diameter or less, since it is preferable to have a plurality of the microspheres to bind to each cell. Also, the slide and morphology of the cells are better maintained with smaller size microspheres. However, larger diameter microspheres can be utilized and a 10 micron diameter non-magnetic microsphere has been utilized. In this case, however, a plurality of cells will bind to each microsphere rather than vice versa.

It appears that the specificity of the procedure of the present invention is sufficiently specific that a single microsphere is indicative that the antigen/receptor is present on the cell. However, to eliminate potential false readings due to coincidence, only cells binding two or more microspheres are deemed to be indicative of the receptor being present. Generally, depending upon the number/concentration of microspheres, more than one microsphere will bind to each cell exhibiting the specified antigen/receptor.

In general, the procedure is as follows:

1. Add well mixed whole blood to an EDTA tube, (i.e. one already containing EDTA), if not collected in EDTA. It is preferred that the blood be collected in EDTA.

2. Add 100 ul of the blood from the EDTA tube to a test tube.

3. Add appropriate microsphere volume to the blood and vortex mixture for approximately 2–3 seconds.

4. Cap the test tube and gently mix for a time sufficient to bind the cells to the microspheres. Times on the order of ten minutes have been found to be sufficient.

5. Following mixing, withdraw an aliquot and make a blood smear. The smear should resemble a peripheral blood smear commonly used for counting differentials.

6. When the slides have dried thoroughly, stain with Wright or Wright/Giemsa stain using the same procedure as for conventional differential slides.

7. View the slide on an immersion oil lens using a 40× or 100× objective noting the cells which have the microspheres attached to them.

8. Qualitative positive results are seen when a specific cell type is consistently tagged with two or more microspheres. The degree of positivity of a cell population for a particular antigen can be reflected in the number of cells of that population which are bound by microspheres.

Suggested microsphere to whole blood ratio according to total white cell count is as follows:

| WBC ct (cells/ul) | Bead Volume (1% soln of 1.17 micron microspheres) |
| --- | --- |
| 0–20,000 | 10 ul |
| 20,001–75,000 | 20 ul |
| more than 75,000 | 30 ul |

If it is desired to deplete the platelets, then the following procedure is utilized to deplete the platelets prior to adding the blood to the test tube in step 2 above.

1. Add 200 microliters EDTA anticoagulated whole blood to a test tube.

2. Add 20 microliters of magnetic PLT-1 microspheres.

3. Mix for a time sufficient to bind the cells to the microspheres. Times of 15 seconds to 2 minutes have been found to be sufficient.

4. Place in magnetic field for 5 minutes.

5. Remove supernatant (whole blood minus microspheres with attached platelets).

6. Use in above procedure at stage 2.

Figure 4:
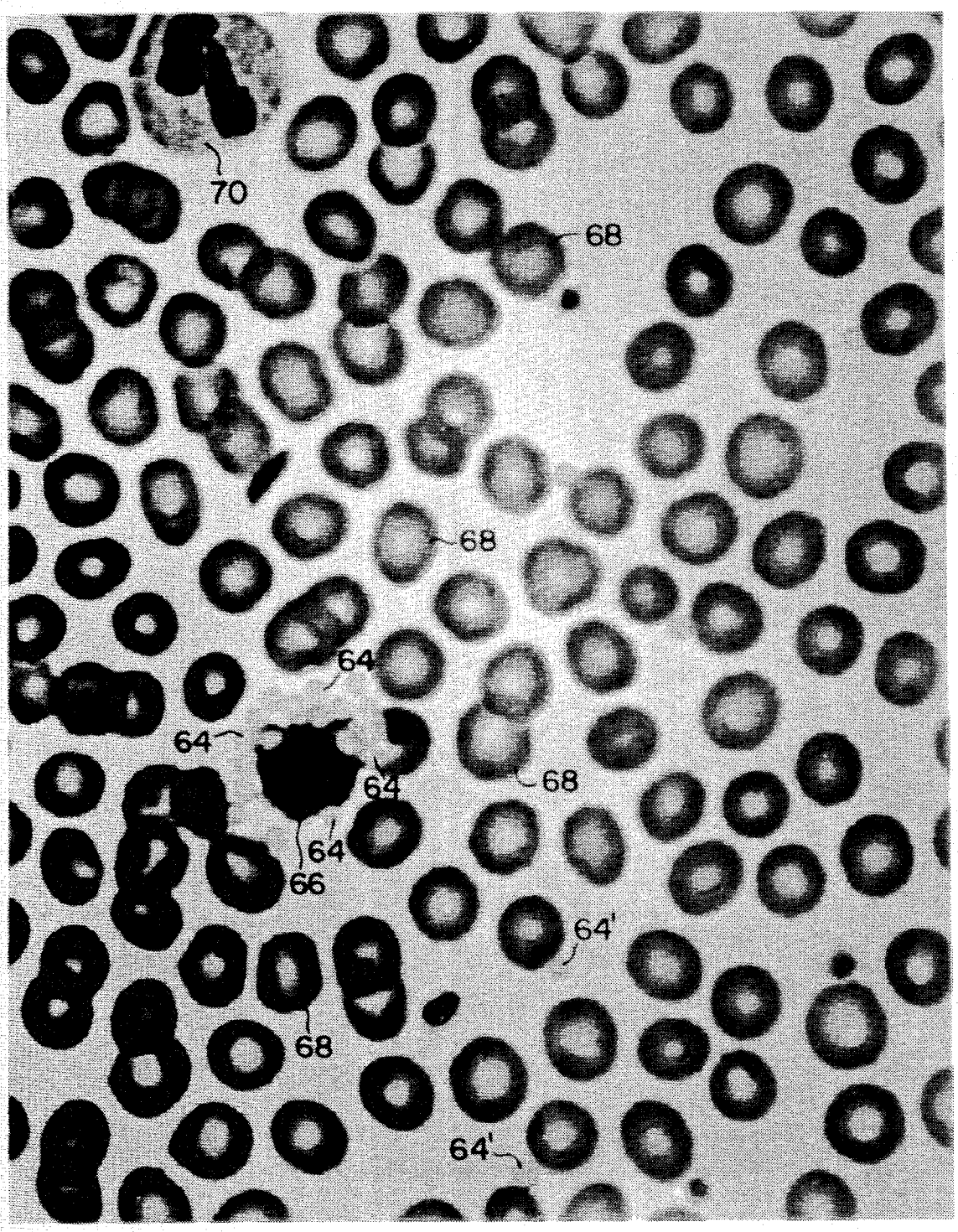
FIG. 4 is a drawing of an optical image of a stained slide illustrating the binding of microspheres to a specific cell antigen.

Utilizing the procedure of the invention, the specificity of CD2 to lymphocytes is illustrated in FIG. 4. A plurality of non-magnetic microspheres 64 having a T11 specific antibody bound thereto are shown bound to a lymphocyte cell 66 on a slide in which the RBC's 68 have not been removed. There are some free (non-bound) T11 microspheres 64'. A neutrophil 70 illustrates the specificity of the T11 microspheres 64, since they do not bind to the neutrophils 70.

The drawings are depicted in black and white in accordance with standard drawing conventions, however, the actual stained slides are in color. In that regard, as is conventional, the various cells are colored as follows:

Neutrophils: Cytoplasm is light pink and the small, numerous granules have a light pink to bluish-black color. The nucleus is dark bluish-purple.

Blasts: Bluish cytoplasm which stains unevenly and nucleus is purple.

Lymphocytes: Cytoplasm is blue, and the nucleus is dark bluish-purple.

Eosinophils: Cytoplasm is obscured by the large spherical granules which stain reddish-orange. The nucleus is dark bluish-purple.

Monocytes: Cytoplasm is grey-blue and the nucleus is dark bluish-purple.

Basophils: Granules are dark purple and nucleus is slightly lighter colored. Granules obscure the cytoplasm.

Red Blood Cells: Cells are red but color is less intense in the middle.

Platelets: Cells are light blue with small bluish granules.

In addition, the magnetic type microspheres are reddish-brown and the non-magnetic microspheres are white. This allows the cells and microspheres to easily be differentiated from one another. The microspheres also can be other colors, sizes and shapes to provide the differentiation, as desired.

Figure 5:
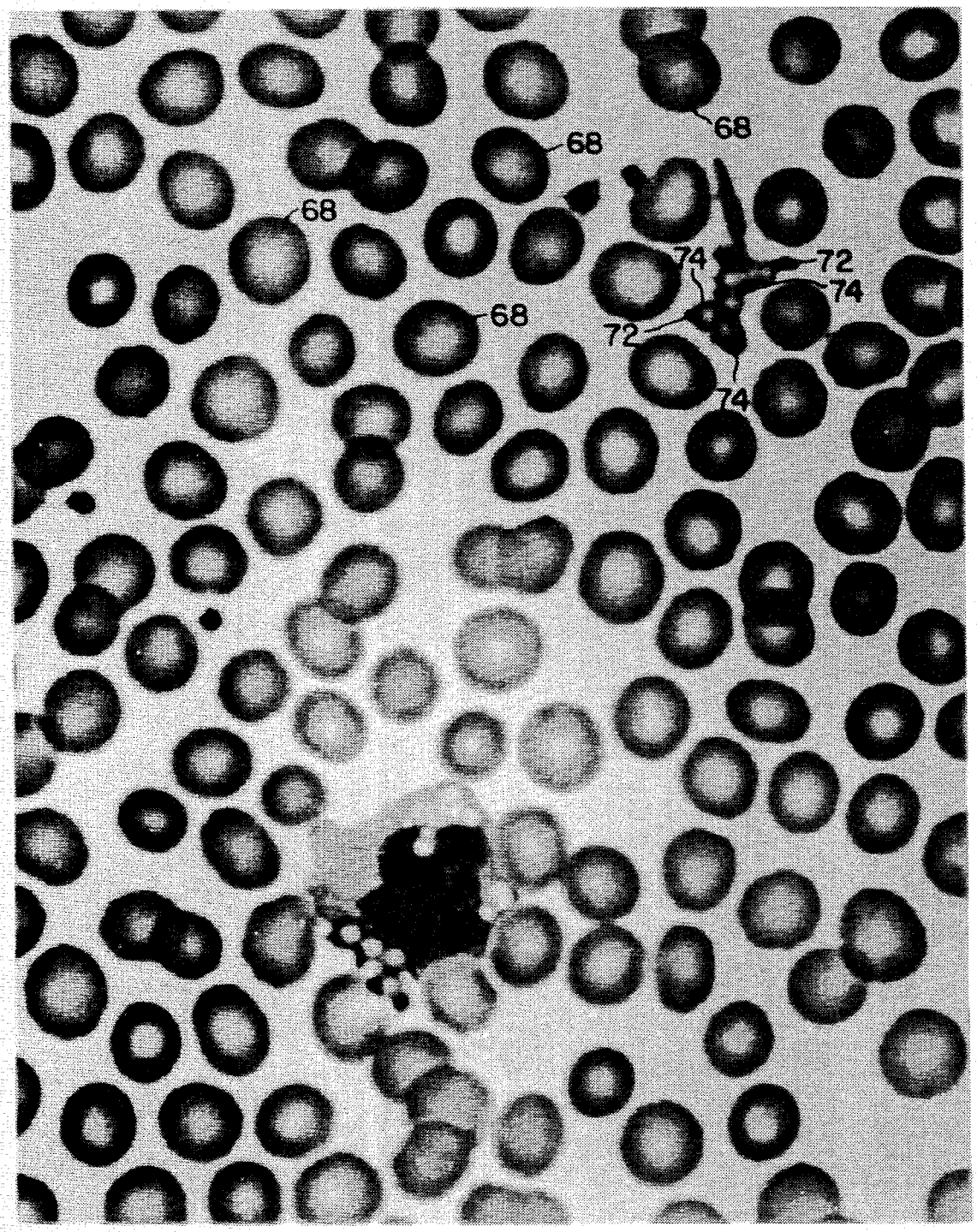
FIG. 5 is a drawing of an optical image of a stained slide illustrating the binding of microspheres to a different specific cell antigen.

Referring to FIG. 5, a plurality of non-magnetic microspheres 72 having a 4B4 specific antibody bound thereto are shown bound to a plurality of platelets 74, which appear to have been clumped together by the microspheres 72. Since the 4B4 specific antibody binds to platelets as illustrated and will also bind to some L's, the platelets are first depleted prior to analyzing a sample for 4B4 type L's.

Figure 6:
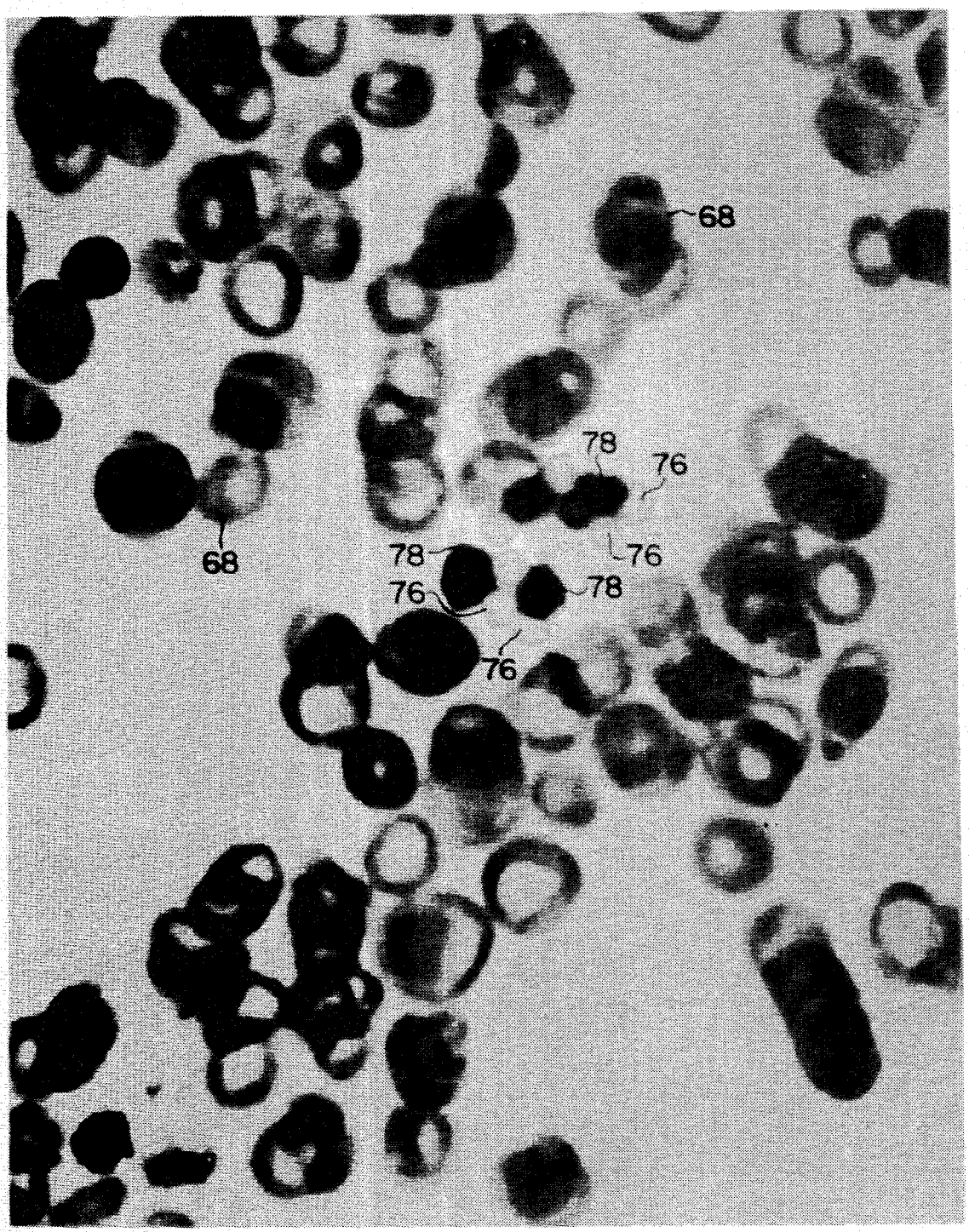
FIG. 6 is a drawing of an optical image of a stained slide illustrating the binding of microspheres to a further different specific cell antigen indicating the type of CLL.

FIG. 6 illustrates a plurality of microspheres 76 having a B1 specific antibody bound thereto bound to lymphocytes 78 which exhibit the presence of B cell CLL. The microspheres 76 are three micron microspheres, whereas the microspheres 64 and 72 are two micron microspheres. This pattern showing a plurality of lymphocytes 78 having microspheres 76 bound thereto is indicative of B cell CLL, since in normal blood very few L's are B1 type lymphocytes.

Figure 7:
FIG. 7 is a drawing of an optical image of a stained slide illustrating the non-binding of microspheres to another specific cell antigen, further differentiating the type of CLL.

Referring to FIG. 7, the lymphocytes 78 again were mixed in another sample portion with a plurality of microspheres 80 having a J5 specific antibody bound thereto. The microspheres 80 will bind to some types of CLL and hence the non-binding of the microspheres 80 (two free ones of which are shown adjacent one RBC 68), indicates that the lymphocytes 78 exhibit the absence of CALLA to which J5 does bind.

Figure 8:
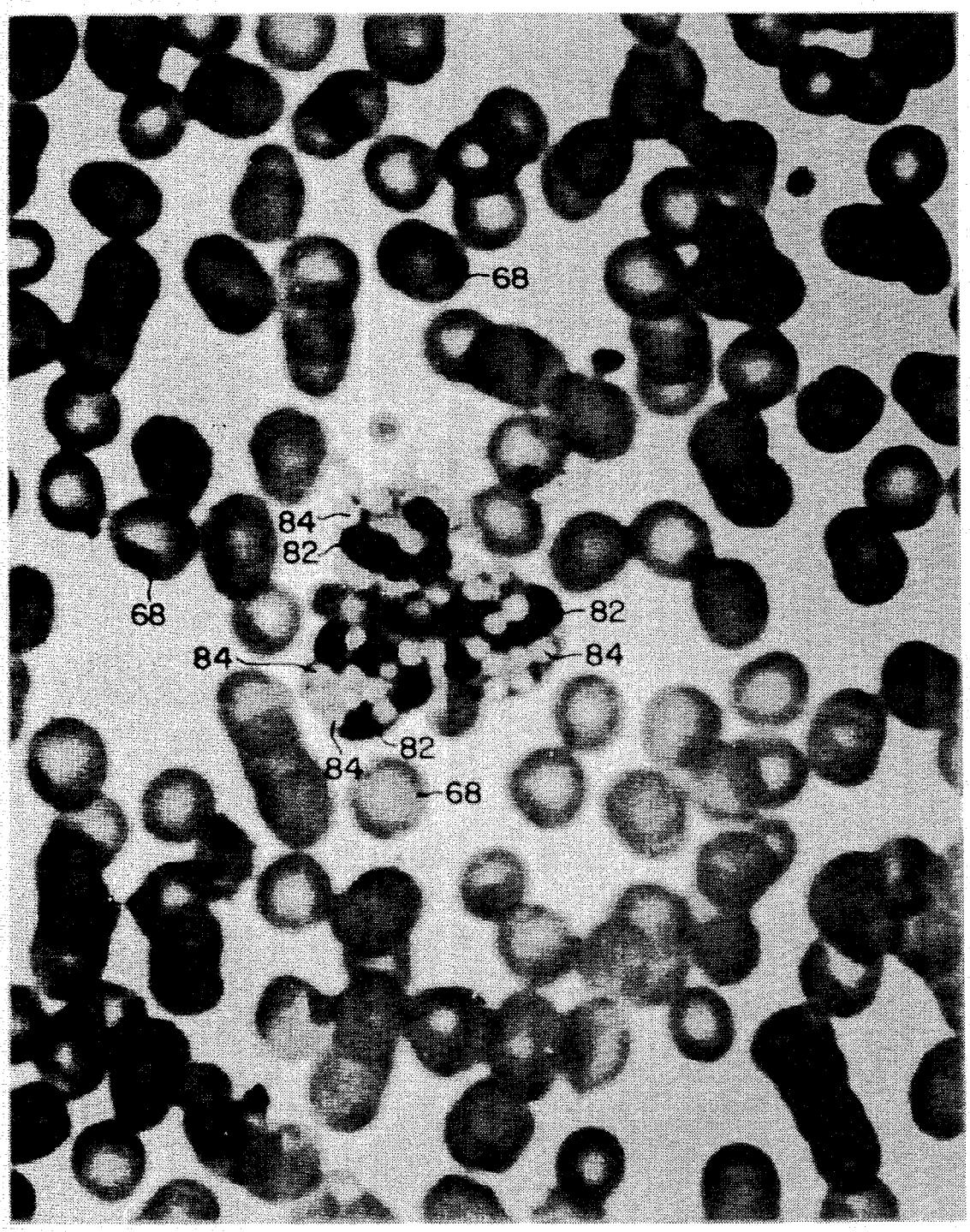
FIG. 8 is a drawing of an optical image of a stained slide illustrating the binding of microspheres to a specific cell antigen on a neutrophil.

FIG. 8 illustrates three neutrophils 82, each having a plurality of microspheres 84 having an N and E specific antibody bound thereto, such as previously referenced. This illustrates the specificity of the N and E microspheres to the neutrophils 82. In each of the examples, the whole slide or a major portion thereof was traversed to ascertain that the microspheres do not bind to any other WBC's, other than those to which they are specific.

Figure 9:
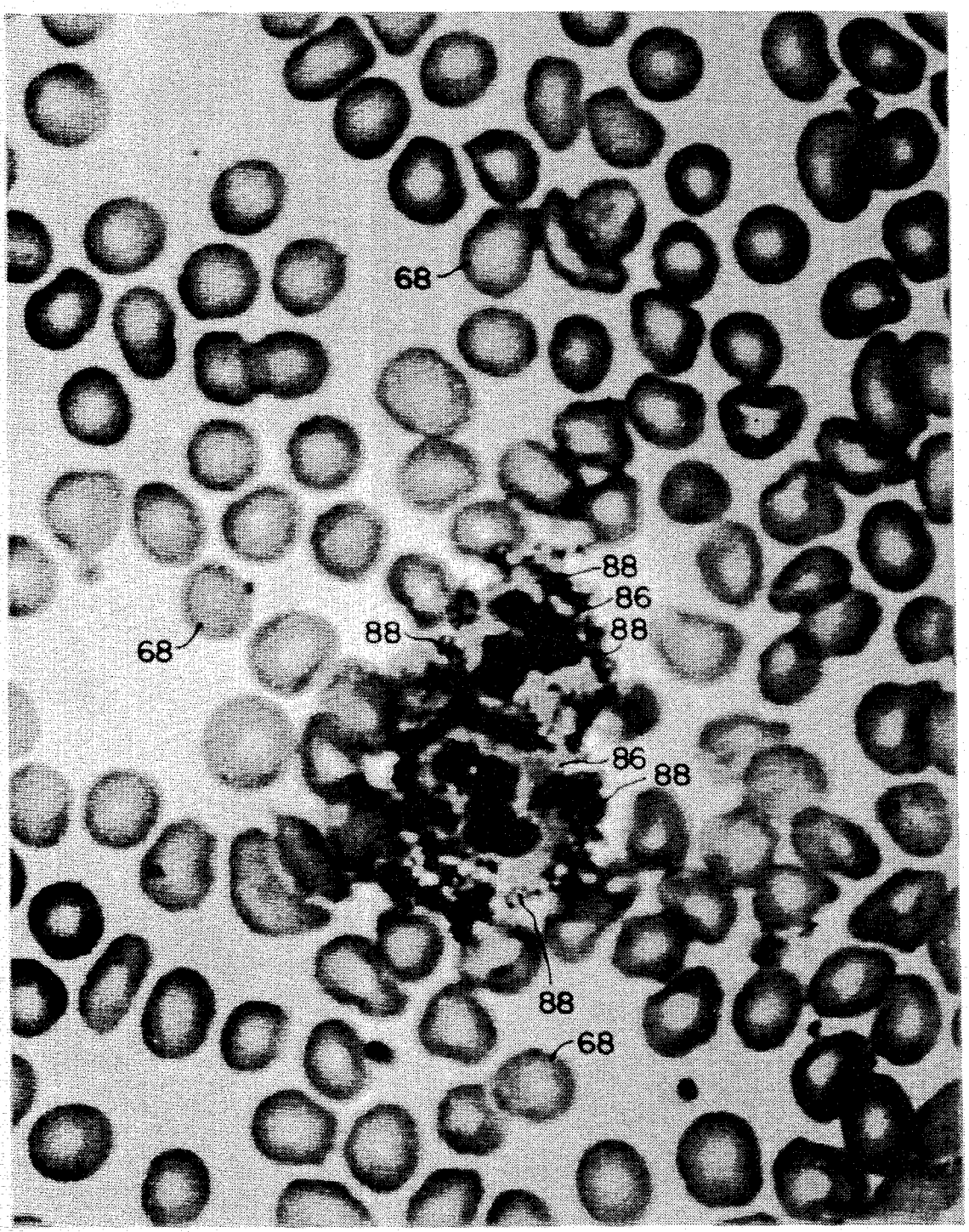
FIG. 9 is a drawing of an optical image of different colored microspheres illustrating the binding of microspheres to another specific cell antigen on neutrophils.

FIG. 9 illustrates two neutrophils 86, each having a plurality of microspheres 88 bound thereto. The microspheres 88 again having an N and E specific antibody bound thereto. In this case, the microspheres are magnetic on the order of one micron diameter and whereas the non-magnetic microspheres appear white in color on the slides, the magnetic microspheres 88 appear brownish in color and can be differentiated in color from the non-magnetic microspheres as well as in size.

Figure 10:
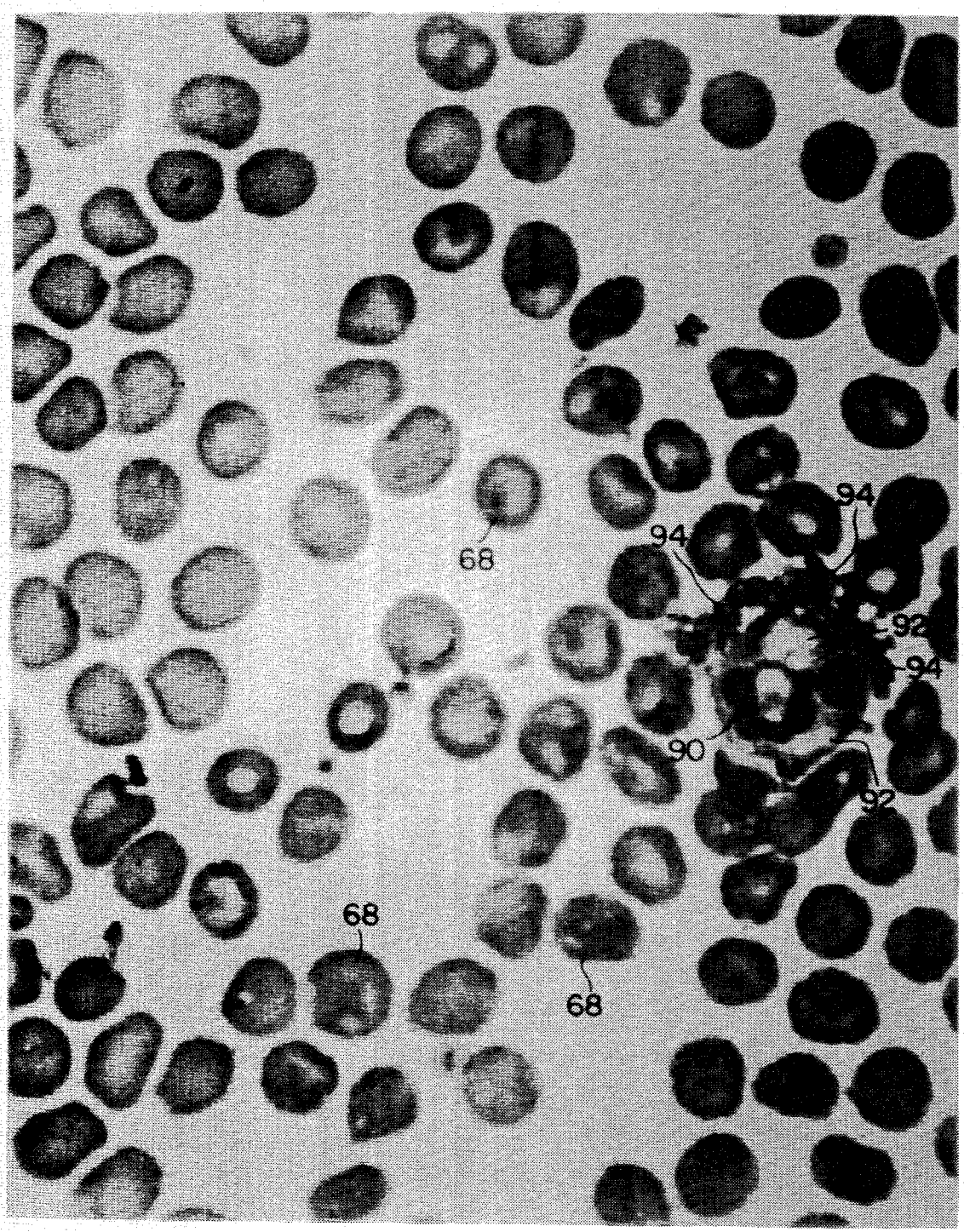
FIG. 10 is a drawing of an optical image of both the different colored and different sized microspheres of FIGS. 8 and 9 illustrating the binding of different microspheres to different cell antigens on neutrophils.

This differentiation is best illustrated in FIG. 10, where a single neutrophil 90 is illustrated having a plurality of two micron non-magnetic white microspheres 92 bound thereto, with the microspheres 92 having an N specific antibody bound thereto, such as previously referenced. The neutrophil 90 also has a plurality of one micron magnetic brownish microspheres 94 bound thereto, with the microspheres 94 having an N and E specific antibody bound thereto. This allows a specific cell to be identified as having two or more antigens of interest simultaneously identified.

The RBC's generally would not be removed as is illustrated in FIGS. 4–10. The smears illustrated in FIGS. 4–10 are prepared in the conventional way of viewing blood cells, with all cells present. Further, cytocentrifugation can damage the cell morphology, especially abnormal cells and hence is not preferred. However, it can be most convenient to remove the RBC's when only a very low WBC count on the order of about 1000–2000 WBC's/ul or less are present. The concentration of the WBC's greatly facilitates their observation. The RBC's should be removed in the least damaging manner so as least to affect the remaining cell morphology.

One preferable manner of removing the RBC's is by adding a lyse to the sample followed by a quench. The lyse preferably can be a mixture of citric acid monohydrate at a concentration of approximately 0.21 percent (w/v) and saponin at a concentration of approximately 0.02 percent (w/v). The quench preferably can be an aqueous solution of sodium chloride at a concentration of approximately 2.9 percent (w/v) and sodium bicarbonate at a concentration of approximately 0.59 percent (w/v). A bacteriostatic agent, for example, sodium azide at a concentration of approximately 0.01 percent (w/v) is recommended, but not required for performance of both the lyse and quench.

In general, utilizing the above lyse and quench, the procedure is as follows:

1. Add 100 ul of EDTA whole blood to a test tube.
2. Add appropriate microsphere volume to the blood, for example 40 ul of microspheres at $2\times10^7$/ml.
3. Mix gently for a time sufficient to bind the cells to the microspheres, for example on the order of ten to thirty minutes.
4. Remove 35 ul of the mixture and add to a 12× 75 mm tube.
5. Add 500 ul of the lyse and vortex slightly.
6. Immediately add 250 ul of the quench.
7. Incubate for about one minute.
8. Add buffer of 100 ul, 5 percent BSA in PBS, if desired.
9. Add 400 ul of the mixture in the cytocentrifugation device and spin at 500 rpm for 5 minutes to spin the cells onto the slide.
10. Step 10 is the same as steps 6–8 of the procedure set forth on pages 17 and 18.

The RBC's also can be removed utilizing magnetic microspheres as previously described.

Figure 11:
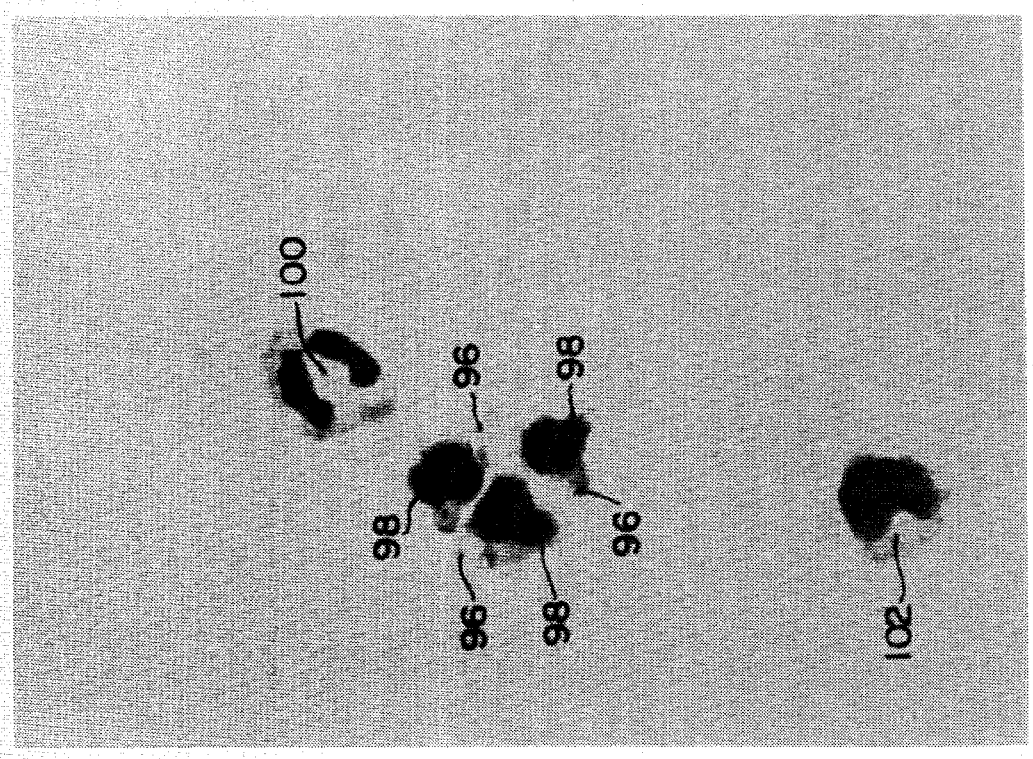
FIG. 11 is a drawing of an optical image of the binding of microspheres to a specific cell antigen on one type of cell and the non-binding to antigens on other types of cells.

FIG. 11 illustrates a cytocentrifugation slide which has been depleted of all cells other than the WBC's. The RBC's if present and other cells if desired are removed and then the remaining cells are spun down onto the slide to concentrate the cells and remove excess moisture. This can facilitate the observation of the cells of interest, which can be a relatively small number in a whole blood sample and hence hard to locate. FIG. 11 illustrates a plurality of microspheres 96 having a T11 specific antibody bound thereto, which microspheres 96 are bound to three lymphocytes 98. The microspheres 96 are not bound to a neutrophil 100 or a monocyte 102, which were also exposed to the microspheres 96.

Figure 12:
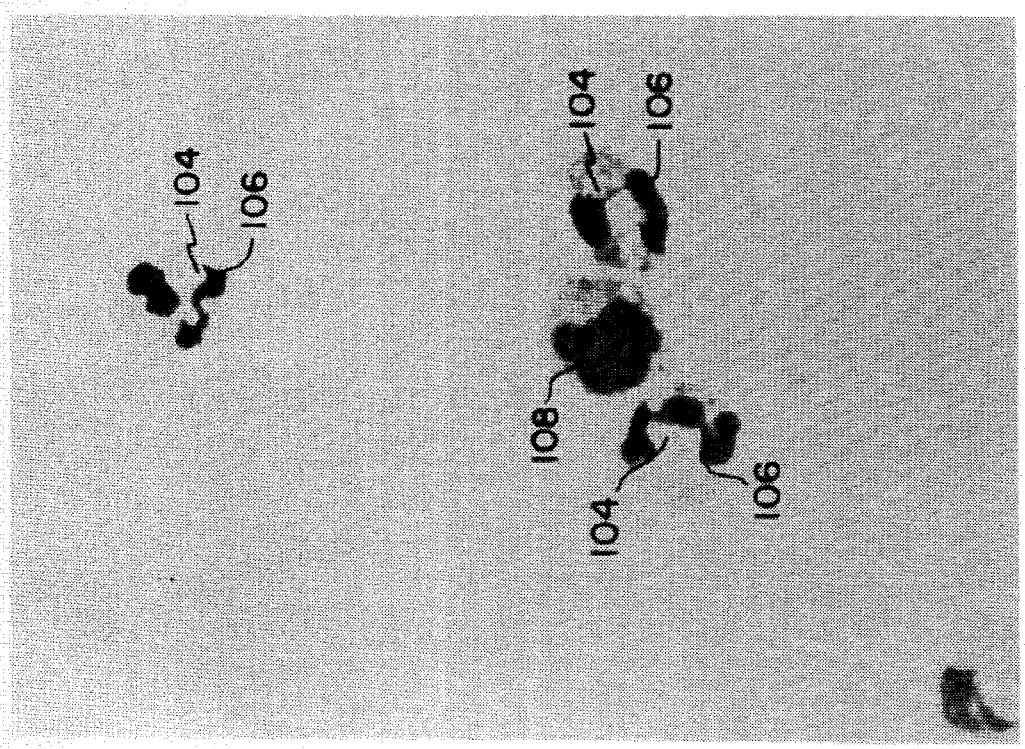
FIG. 12 is a drawing of an optical image of a stained slide illustrating the binding of microspheres to a different specific cell antigen on one type of cells and the non-binding to antigens on other types of cells.

FIG. 12 is another cytocentrifugation prepared slide, which illustrates a plurality of microspheres 104 having an N and E specific antibody bound thereto, which microspheres 104 are bound to several neutrophils 106 and are not bound to a monocyte 108.

Although specific examples have been illustrated utilizing microspheres which are differentiated by size and color, the microspheres also can be differentiated by being of different shapes.

Two further phenomena have been observed in practicing the present invention. These are rimming and slide agglutinations, which both can be called cell clumping. Rimming occurs in some whole blood samples with a high number of cells positive for a specific antigen. The phenomena has been observed during the mixing or incubation period of the whole blood with the microspheres in a reaction vessel, such as a test tube. The positive cells and microspheres tend to aggregate along the outer surface of the whole blood forming a microscopic rim on the test tube. This rim is only seen in samples which are positive. A similar agglutination phenomena has also been observed on a microscopic glass slide. By placing a drop of whole blood on the slide and mixing it with a drop of antibody-coated latex beads by gently rocking the slide, a macroscopic agglutination can be seen in samples with a high number of cells positive for that specific corresponding antigen. This agglutination appears as white clumps with the red blood background on the slide, visual to the naked eye.

These agglutinations can provide a fast screening procedure for high WBC counts under appropriate conditions. These phenomena have been observed with total WBC cell counts on the order of 40–50,000 cells or greater per microliter as contrasted to a normal WBC cell range of 4–11,000 cells per microliter. Although the cell clumping can be visually observed without aid, a microscopic instrument operated manually or automatically or other optical device, can be utilized. Further, rimming can be visually observed manually or automatically optically by scanning the mixing vessel with a light beam which will cause a diffraction pattern when rimming occurs.

Figure 13:
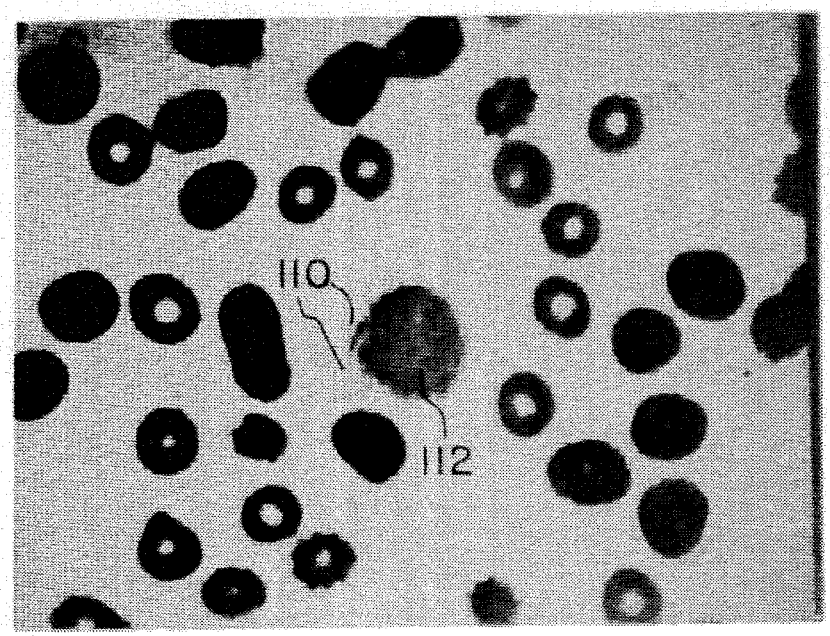
FIG. 13 is a drawing of an optical image of a stained slide illustrating the binding of microspheres having a second reactant bound thereto bound to a first reactant which binds to a specific cell antigen on the cells.

FIG. 13 illustrates a plurality of microspheres 110 having a second reactant bound thereto, which second reactant binds to a first reactant, which first reactant in turn binds to a specific molecule on a cell 112. In this case the cell expresses the CD34 antigen, which the first reactant binds to. The first reactant, for example HPCA-1, is not readily available in the proper concentration to be bound directly to the microsphere 110. Therefore, a second reactant, here a goat anti-mouse antibody, is bound to the microspheres. The second reactant will bind to any mouse antibody and thus the microspheres 110 will bind to the first reactant bound to the microspheres on the cells 112. The first reactant and microsphere 110 bound to the second reactant also could be combined with the sample simultaneously. Alternatively, the first reactant could be bound to the second reactant on the microspheres 110 and then the microspheres 110 with the second reactant bound thereto and the first reactant bound also thereto via the first reactant then can be combined with the sample. The first reactant bound to the cell 112 alone, without the microspheres 110, is not visually or microscopically differentiable.

In general, the first procedure is as follows:

1. Step 1 is the same as steps 1 and 2 of the previous procedure set forth on pages 17 and 18.

2. Add 10 ul of the first reactant and vortex mixture for approximately 2–3 seconds.

3. Incubate mixture for about 10 minutes.

4. Add 10 ul of microsphere with the second reactant bound thereto.

5. Step 5 is the same as steps 4–8 of the procedure set forth on pages 16 and 17.

The other types of procedures illustrated with respect to FIGS. 5–12, can also be utilized with the type of reactant binding described with respect to FIG. 13. Other sets of microspheres with different reactants can be added to a second sample portion, the microspheres being of different sizes and/or colors to be differentiated therebetween. One or more different sets of microspheres with different reactants also can be combined with the first and second reactants in the first sample portion. In this procedure, however, the other reactants must be of a different type than the second reactant, otherwise the microspheres also will bind to the second reactant. For example where the second reactant is an anti-mouse antibody, the other reactants could be a swine, rabbit or other different antibody type.

Different procedures as described with respect to FIG. 13 were attempted to ascertain the effects of the various methods. As a first example, 5 ul of T4 antibody were added to 2.00 ul of whole blood by gently vortexing. The mixture was left to stand or incubate for 10 minutes. After incubation, 10 ul of microspheres were added, vortexed gently and mixed on a roller rocker for 10 minutes, after which a smear was made as above described. This resulted in the usual binding of the microspheres to the L's, two examples being 37 and 44 percent.

In a second example the microspheres and T4 antibody were added at the same time and roller rocked for 10 minutes before preparing a slide. This resulted in a somewhat decreased percentage of 28 and 31, for two examples.

As a third example, the microspheres were added and mixed without any antibody, before mixing and making the slide. In this example, as expected, no binding of the microspheres to the cells was found.

In another example, the T4 antibody was roller rocked for 10 minutes with the sample, then the microspheres were added and also mixed for 10 minutes, then the slide was prepared. This resulted in a normal percent of 36.

As a final example, the microspheres and T4 antibody were mixed together and left to stand for 10 minutes. This mixture then was added to the sample portion and mixed 10 minutes prior to preparing the slide. The percent obtained 23 and 27 were somewhat lower. One explanation is that some of the antibody remained free in the mixture and blocked some of the sites to which the microspheres would have bound.

Figure 14:
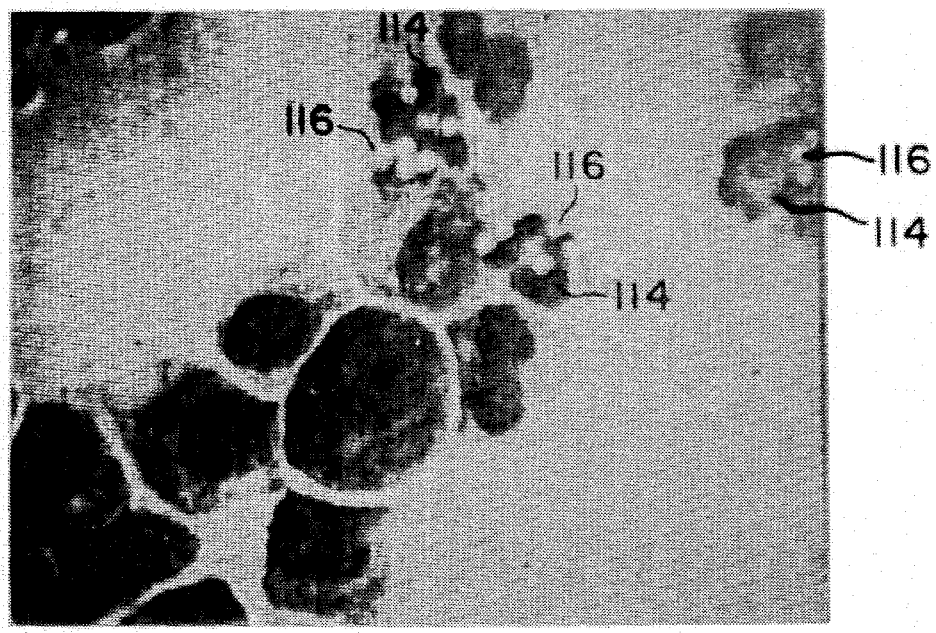
FIG. 14 is a drawing of an optical image of a stained slide illustrating the binding of microspheres to a specific cell antigen on a neutrophil in bone marrow.

FIG. 14 illustrates several neutrophils 114 in a bone marrow sample, each having a plurality of microspheres 116 bound thereto. The microspheres 116 have an N specific antibody bound thereto. This example illustrates the effectiveness of the procedure in other types of fluids other than blood, here bone marrow.

Figure 15:
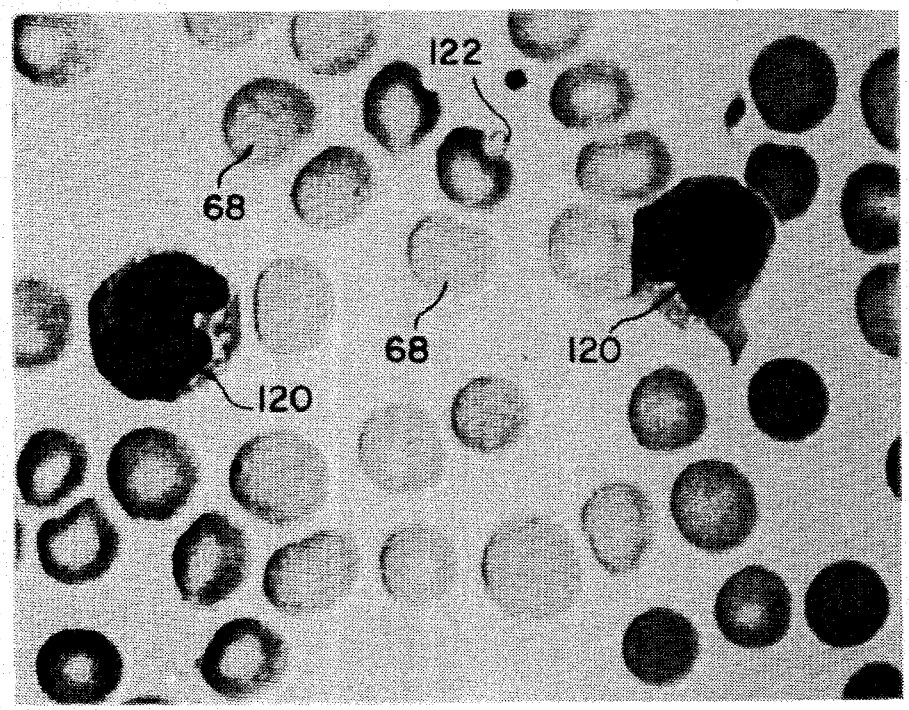
FIG. 15 is a drawing of an optical image of a stained slide illustrating the non-binding of microspheres to a first specific cell antigen in a suspected HTLV-1 sample.
Figure 16:
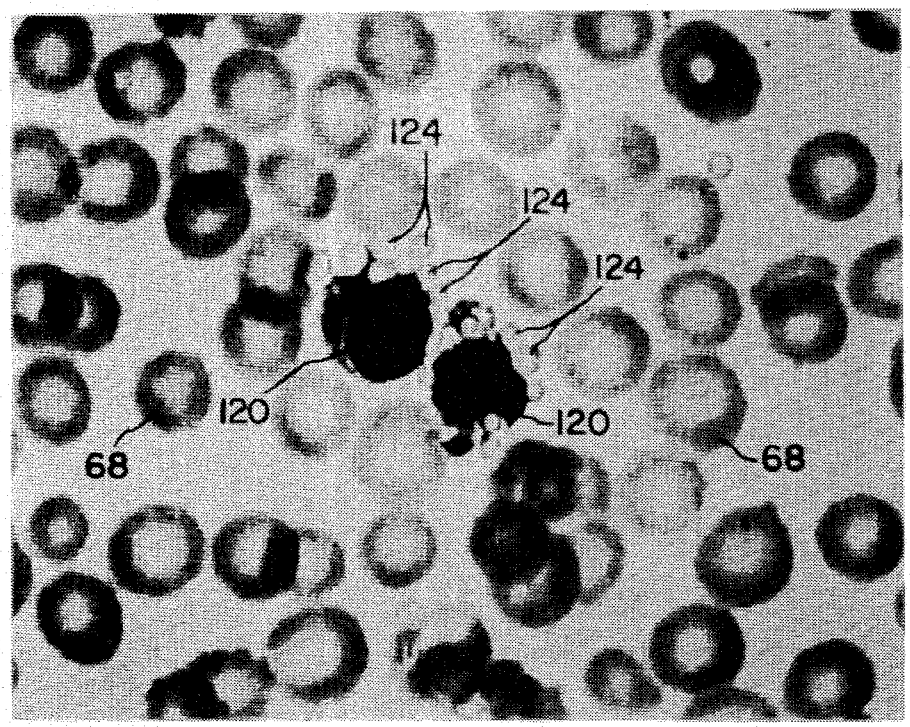
FIG. 16 is a drawing of an optical image of a stained slide illustrating the binding of microspheres to a second specific cell antigen in the suspected HTLV-1 sample depicted in FIG. 15.

Referring now to FIGS. 15 and 16, further examples of the present invention are illustrated.

The methodology of the parent application is equally applicable to the screening of cancer cells as referred to therein and as described herein after in more specific detail. The cells of various types of cancer express different specific molecules, which allow the utilization of specific monoclonal antibodies to assist in differentiating between various types of cancer. This differentiation can be extremely critical, because time can be critical and different types of cancer require different treatments.

Further, merely staining the cells and viewing the cell morphology may not be sufficient to determine the type of specific cancer. Alternatively, the pathologist may desire further information to confirm the morphological evaluation. If such information is desired, generally a flow cytometry instrument with fluorescent monoclonal antibodies is utilized to provide the information One such flow cytometry monoclonal antibody panel is illustrated in Table II.

TABLE II

| Leukemia/Lymphoma Immunophenotyping Panel Association/Restriction | | | |
|---|---|---|---|
| MAb | B-Cell | T-Cell | Myelomonocytic |
| HLA-DR | + | −[a] | +[b] |
| CD19 | + | − | − |
| CD10 | +[c] | − | − |
| CD20 | +[d] | − | − |
| CD2 | − | + | − |
| CD5 | −[e] | + | − |
| CD7 | − | + | −[f] |
| CD13 | − | − | + |

TABLE II-continued

Leukemia/Lymphoma Immunophenotyping Panel
Association/Restriction

| MAb | B-Cell | T-Cell | Myelomonocytic |
|---|---|---|---|
| CD33 | – | – | + |
| CD14 | – | – | +[g] |

[a]Post-thymic T cell malignancies are usually HLA-DR[+] whereas T-cell acute leukemias and lymphomas are almost always HLA-DR[–].
[b]HLA-DR is ubiquitous on myeloblasts but absent on progranulocytes. Therefore, monoblasts and their progeny are always HLA-DR[+]; acute progranulocytic leukemia (M3) is almost always HLA-DR[–].
[c]Very frequently, CD10 is positive in follicular lymphomas.
[d]CD20 is less ubiquitously expressed compared with CD19 in acute leukemias as CD20 appears late during ontogeny. However, it is almost always present on B cell lymphomas.
[e]CD5 is coexpressed on a small subpopulation of normal circulating B cells. It is a useful marker to identify chronic lymphocytic leukemia where it is coexpressed on the malignant B cells.
[f]CD7 is present on a small percent of otherwise typical acute myeloid leukemias. It is frequently negative in post-thymic T cell malignancies and therefore its absence is useful in detection of early T cell malignancies.
[g]CD14 is virtually restricted to mature monocytes. Therefore, it is useful to separate monocytes from blasts or monocyte precursors which will usually be HLA-DR positive but CD14 negative.

Table II is taken from a publication by Landay, A. L. and Dugue, R. E. In press, 1991. Hematopoietic Neoplasmas. Manual of Clinical Laboratory Immunology, American Society for Microbiology, Washington, D.C. The Table is illustrated for flow cytometry monoclonal antibody flurochromes utilization, but as previously stated such flow cytometry instruments are not always available, which can cause significant time delays.

Applicants have discovered that the information determination is equally applicable to the utilization of the microspheres of the present invention without a flow cytometry instrument. A panel of different sets of microspheres having various monoclonal antibodies bound thereto can be utilized to provide fast screening information for the type of cancer present in the sample. For example, utilizing a plurality of either optically distinguishable sets of microspheres in one or more smears or a different set of microspheres in each smear or a combination thereof, can provide fast screening information. The plurality or panel of microspheres could include on different sets of microspheres the following monoclonal antibodies:

HLA-DR—such as but not limited to I3

B lymphocyte—such as but not limited to CD19

T-cell—such as but not limited to CD 2

Monocytic—such as but not limited to CD14

Myeloid—such as but not limited to CD33

Applicants also have discovered that KC-48 also appears to provide information on myeloid leukemias.

Utilizing the present invention, a sample obtained from a pathologist which was indicated as being an acute myeloid leukemia (AML) type of cancer was screened for information to confirm that this was indeed an AML cancer. AML is an early cancer with few mature cells, thus the monoclonal antibodies bound to microspheres should bind to immature cells to differentiate the type of cancer cells. This prediction was confirmed by the fast screening panel utilizing separate smears where I3 and KC48 monoclonal antibodies were slightly to moderately positive, i.e., bound to a moderate number of cells in moderate numbers on each cell. The T11 monoclonal antibody microspheres bound to the few mature L's in the sample. The myeloid (here CD34) monoclonal antibody microspheres were only very slightly positive, while the MY4 and B4 monoclonal antibody microspheres were negative, i.e., did not bind to any cells.

If the fast screening panel is conclusive, then the pathologist may decide the treatment regimen without further information. If the fast screening panel is not conclusive then the pathologist could obtain further information, such as from a flow cytometry instrument.

Further information also can be obtained utilizing the present invention, for example, if the original fast screening panel indicates a T-cell positive cancer, then additional slides could be utilized to provide further information. For example, CD4, CD8 and CD10 could then be utilized to further specify the type of cancer. Some of the various types of cancer are the above referenced ALL and AML, chronic lymphocytic leukemia (CLL), and human T-cell lymphotrophic virus-1 (HTLV-1) leukemia. HTLV-1 stained cells may not be morphologically distinguishable from a B-cell cancer, however this difference is very critical. By utilizing microspheres in two separate stained sample portions, or two distinguishable sets of microspheres in one stained slide, the two cancers can be distinguished. As one example, one of the two sets of microspheres can have T4 monoclonal antibodies bound thereto and the second set of microspheres can have T8 monoclonal antibodies bound thereto. If only the T4 set of microspheres bind to the cells, then the cancer most likely is HTLV-1. If the T8 set of microspheres also bind to a majority of the cells, then the cancer probably is not HTLV-1 and the sample would be further analyzed for more information. The pathologist to confirm the HTLV-1 type leukemia could further analyze a serum sample for the presence of HTLV-1 virus.

Referring to FIG. 15, a suspected HTLV-1 cancer sample is illustrated with a pair of cancer cells 120, to which microspheres having a CD8 specific antibody bound thereto were added. One free microsphere 122 is illustrated and the cells 120 clearly do not exhibit binding to the microsphere 122.

FIG. 16 illustrates a pair of the cancer cells 120 in a different sample portion of the suspected HTLV-1 cancer sample illustrated in FIG. 15. In this sample portion, a plurality of microspheres 124 having a CD4 specific antibody bound thereto, clearly are bound to the cells 120. The absence of CD8 specific antibody binding and the presence of CD4 specific antibody binding to the cells 120, provides a strong indication that the cells 120 are HTLV-1 leukemia cells.

If the pathologist has determined that the cancer is a lymphoma type of cancer, then the fast screening panel need only provide information between B-cell and T-cell type lymphomas.

Another method of providing fast cancer screening information is to utilize magnetic microspheres and after binding, to magnetically deplete the bound cells. In this example, a standard smear first would be made without microspheres for a reference smear. The second magnetically depleted smear then would be compared to the reference smear. If, the morphological cells of interest or a considerable portion thereof were removed, then the cancer or some of the cells would be positive to the type of monoclonal antibodies utilized with the microspheres. In this case, separate depleted smears would be utilized for each monoclonal antibody desired to be screened.

We claim as our invention:

1. A method of optically screening microscopic cells for cancer, comprising:

providing one of a whole blood or a bone marrow sample including all originally present constituents or a portion thereof including at least a plurality of cells of interest unaltered in number and type with at least some cells appearing to be cancer cells;

combining at least a first sample portion of said cells with at least a first set of microspheres having at least a first reactant bound thereto specific to at least a first specific molecule which can exist on at least one type of cancer cell, said first set of microspheres being smaller than said cells to which said microspheres are bound;

preparing a smear of said cells on a slide including said microspheres;

staining said smear with a histological type stain; and optically viewing at least some of said cells with a microscope to at least identify the presence or absence of cells to which said first set of microspheres are bound to provide cancer screening information.

2. The method as defined in claim 1 including providing a whole blood sample or a portion thereof and staining said smear with a Wright-type stain.

3. The method as defined in claim 2 wherein said first reactant is an antibody specific to at least said first specific molecule which is a first cell antigen.

4. The method as defined in claim 2 including adding a chelating agent to said sample to prevent the neutrophil population from ingesting said microspheres.

5. The method as defined in claim 2 including image analyzing said smear.

6. The method as defined in claim 2 including morphologically characterizing at least some of said cells and including identifying the presence or absence of bound microspheres on said characterized cells.

7. The method as defined in claim 1 including image analyzing said smear.

8. The method as defined in claim 1 including combining said first portion of said cells with at least a second set of microspheres having at least a second reactant bound thereto specific to at least a second specific molecule which can exist on at least one type of cell, said second set of microspheres having a different optical characteristic from said first set of microspheres and optically viewing at least some of said cells with a microscope to at least identify the presence or absence of cells to which said second set of microspheres are bound.

9. The method as defined in claim 8 including concurrently combining said first portion of said cells with at least said first and second set of microspheres.

10. The method as defined in claim 8 wherein said first and second set of microspheres are physically different in size.

11. The method as defined in claim 10 including said second set of microspheres being substantially smaller than said first set of microspheres.

12. The method as defined in claim 8 wherein first and second set of said microspheres are optically different in color.

13. The method as defined in claim 1 including combining at least a second portion of said cells with at least a second set of microspheres having at least a second reactant bound thereto specific to at least a second specific molecule expected to exist on at least a second type of cancer cell;

preparing a smear of said cells on a slide including said microspheres;

staining said smear with a histological type stain; and optically viewing at least some of said cells with a microscope to at least identify the presence or absence of cells to which said second set of microspheres are bound.

14. The method as defined in claim 13 wherein said first and second set of said microspheres are physically different in size.

15. The method as defined in claim 13 wherein first and second set of said microspheres are optically different in color.

16. The method as defined in claim 13 wherein said first reactant is a CD4 monoclonal antibody and said second reactant is a CD8 monoclonal antibody and the presence or absence of cells to which said CD4 and CD8 monoclonal antibody microspheres are bound is indicative of HTLV-1 leukemia.

17. The method as defined in claim 1 including combining a plurality of different portions of said cells each with a different set of microspheres, each set having different reactants bound thereto specific to different specific molecules expected to exist on different types of cancer cells;

preparing separate smears of said different cell portions on separate slides including said microspheres;

staining each said smear with a histological type stain; and optically viewing at least some of said cells on each said smear with a microscope to at least identify the presence or absence of cells to which said sets of microspheres are bound to provide a fast cancer screening panel.

18. The method as defined in claim 1 including combining said first portion of said cells with a plurality of sets of microspheres, each set having a different reactant bound thereto specific to a different specific molecule which can exist on at least one type of cancer cell, each of said sets of microspheres having different optical characteristics from one another and optically viewing at least some of said cells with a microscope and at least identifying the presence or absence of cells to which said different sets of microspheres are bound.

19. The method as defined in claim 18 including concurrently combining said first portion of said cells with said plurality of sets of microspheres.

20. The method as defined in claim 18 wherein each of said sets of microspheres are physically different in size or color.

21. The method as defined in claim 1 including providing a whole blood sample or a portion thereof and morphologically characterizing at least some of said cells, including identifying the presence of a plurality of bound microspheres on said characterized cells.

22. The method as defined in claim 1 including mixing said first portion of said cells with said first set of microspheres.

23. A method of optically screening microscopic cells for cancer, comprising:

providing one of a whole blood or a bone marrow sample including all originally present constituents or a portion thereof including at least a plurality of cells of interest unaltered in number and type with at least some cells appearing to be cancer cells;

preparing a first smear of a first unmodified sample portion of said cells on a slide;

staining said first smear with a histological type of stain;

optically viewing at least some of said cells with a microscopic to at least identify the presence of potential cancer cells;

combining at least a second sample portion of said cells with at least a set of microspheres having at least a first reactant bound thereto specific to at least one specific molecule which can exist on at least one type of cancer cell;

removing said set of microspheres with any cells which are bound to said microspheres from said second portion;

preparing a second smear of said cells on a slide;

staining said second smear with a histological type of stain; and optically viewing at least some of said second portion cells on said second smear and comparing said second smear to said first smear to identify the presence or absence of said potential type of cancer cell.

24. A method of optically screening microscopic cells for cancer, comprising:

providing one of a whole blood or bone marrow sample including all originally present constituents or a portion thereof including at least a plurality of cells of interest unaltered in number and type with at least some cells appearing to be cancer cells;

combining at least a first sample portion of said cells with a first reactant specific to at least a first specific molecule which can exist on at least one type of cancer cell;

combining said first sample portion of said cells with at least a first set of microspheres having at least a second reactant bound thereto which will bind to said first reactant, said first set of microspheres being smaller than said cells to which said microspheres are bound;

preparing a smear of said cells on a slide including said microspheres;

staining said smear with a histological type stain; and optically viewing at least some of said cells with a microscope to at least identify the presence or absence of cells to which said first set of microspheres are bound to provide cancer screening information.

25. The method as defined in claim 24 including providing a whole blood sample or a portion thereof including at least one WBC population and staining said smear with a Wright-type stain.

26. The method as defined in claim 25 wherein said first reactant is an antibody specific to at least said first specific molecule which is a first cell antigen and said second reactant is an antibody which will bind to said first reactant antibody.

27. The method as defined in claim 25 including adding a chelating agent to said sample to prevent the neutrophil population from ingesting said microspheres.

28. The method as defined in claim 25 including morphologically characterizing at least some of said cells and including identifying the presence or absence of bound microspheres on said characterized cells.

29. The method as defined in claim 24 including image analyzing said smear.

30. The method as defined in claim 24 including combining said first portion of said cells with at least a second set of microspheres having at least a third reactant bound thereto specific to at least a second specific molecule which can exist on at least a second type of cancer cell, said second set of microspheres having a different optical characteristic from said first set of microspheres and optically viewing at least some of said cells with a microscope to at least identify the presence or absence of cells to which said second set of microspheres are bound, said third reactant formed from a type which will not bind to said second reactant.

31. The method as defined in claim 30 including concurrently combining said first portion of said cells with at least said first and second set of microspheres.

32. The method as defined in claim 31 wherein said first and second set of said microspheres are physically different in size.

33. The method as defined in claim 32 including said second set of microspheres being substantially smaller than said first set of microspheres.

34. The method as defined in claim 30 wherein first second set of said microspheres are optically different in color.

35. The method as defined in claim 24 including combining at least a second portion of said cells with at least a second set of microspheres having at least a third reactant bound thereto specific to at least a second specific molecule expected to exist on at a second type of cancer cell;

preparing a smear of said cells on a slide including said microspheres;

staining said smear with a histological type stain; and optically viewing at least some of said cells with a microscopic to at least identify the presence or absence of cells to which said second set of microspheres are bound.

36. The method as defined in claim 35 wherein said first and second set of said microspheres are physically different in size.

37. The method as defined in claim 36 including said second set of microspheres being substantially smaller than said first set of microspheres.

38. The method as defined in claim 35 wherein first and second set of said microspheres are optically different in color.

* * * * *